United States Patent [19]
Takenaka et al.

[11] Patent Number: 5,650,982
[45] Date of Patent: Jul. 22, 1997

[54] PULSIMETER PROVIDED WITH OR WITHOUT A PEDOMETER

[75] Inventors: Masaaki Takenaka; Manabu Yoshimura, both of Kyoto; Tsutomu Yamasawa; Maki Hasegawa, both of Osaka; Masatsugu Hirano, Kyoto; Satoshi Nishida, Nara, all of Japan

[73] Assignee: Omron Corporation, Kyoto, Japan

[21] Appl. No.: 631,048

[22] Filed: Apr. 12, 1996

Related U.S. Application Data

[63] Continuation of Ser. No. 383,504, Feb. 2, 1995, Pat. No. 5,539,706.

[30] Foreign Application Priority Data

Feb. 3, 1994 [JP] Japan ......................................... 7-11434

[51] Int. Cl.$^6$ .............................. G04B 47/00; A61B 5/02
[52] U.S. Cl. ................... 368/10; 368/11; 128/677; 128/690
[58] Field of Search ................. 368/10, 11, 276, 368/278, 72–74, 107–113; 340/309.1, 309.4, 323; 364/561, 565, 705, 710

[56] References Cited

U.S. PATENT DOCUMENTS

| | | | |
|---|---|---|---|
| 3,858,574 | 1/1975 | Page | 128/205 T |
| 4,305,401 | 12/1981 | Reissmueller et al. | 128/690 |
| 4,353,152 | 10/1982 | O'Connor et al. | 128/689 |
| 4,407,295 | 10/1983 | Steuer et al. | 128/670 |
| 4,425,921 | 1/1984 | Fujisaki et al. | 128/690 |
| 5,218,966 | 6/1993 | Yamasawa | 128/677 |

*Primary Examiner*—Vit W. Miska
*Attorney, Agent, or Firm*—Fish & Richardson P.C.

[57] ABSTRACT

A pulsimeter having an improved pulse measurement accuracy by having a good shading is provided. The pulsimeter include a main body 2, a finger insertion section 4 disposed on the main body to be inserted by a finger (FIG. 2), a pulse sensor 5 for sensing pulses of a finger inserted into the finger insertion section 4 (FIG. 2), and a display 6 for displaying the pulses sensed by the pulse sensor 5. The finger insertion section 4 is disposed on a surface (the reverse side of the main body 2) opposite to a surface provided with the display 6.

1 Claim, 8 Drawing Sheets

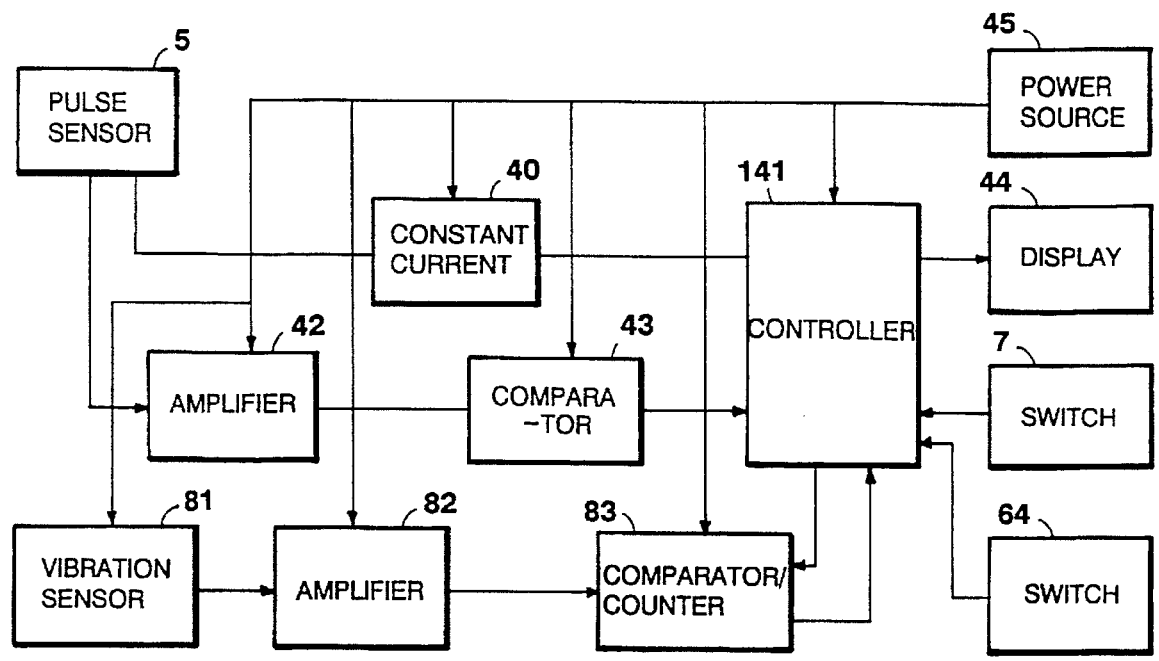
FIG. 12
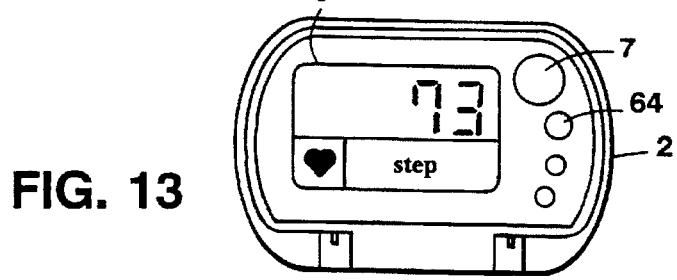
FIG. 13
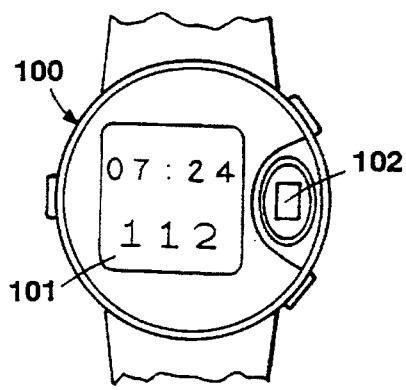   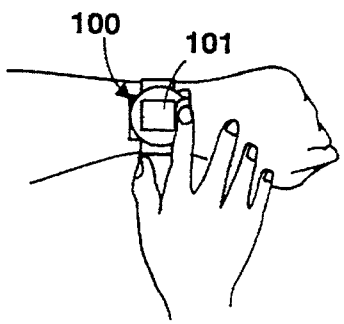
FIG. 14a            FIG. 14b

PULSIMETER PROVIDED WITH OR WITHOUT A PEDOMETER

This application is a continuation of U.S. application Ser. No. 08/383,504, filed Feb. 2, 1995, now U.S. Pat. No. 5,539,706.

BACKGROUND OF THE INVENTION

1. Field of the Invention

This invention relates to a pulsimeter for portable use, and more particularly to an improved pulsimeter provided with a pedometer.

2. Discussion of the Related Art

Referring to FIGS. 14 and 15, there are shown conventional pulsimeters. Such a pulsimeter 100 of FIG. 14 (a) is a wristwatch provided with a pulse measuring function, which includes a display 101 on the face thereof for displaying a clock and the number of measured pulses, and a pulse sensor 102 having light emitting and receiving elements to be touched by a finger. As the pulsimeter 100 is put on a wrist and a finger is put on the pulse sensor 102 as shown in FIG. 14 (b), a series of pulses are detected from the finger and the number of the detected pulses are displayed on display 101.

A pulsimeter 110 shown in FIG. 15(a) on a front side thereof is provided with a display 111, providing a wristwatch and a pulsimeter. The pulsimeter is connected with a finger cuff 112 wrapped around a finger so that pulses can be measured by a pulse sensor 113 disposed on the finger cuff 112 in FIG. 15 (b).

The pulse sensor sections of pulsimeters 100 and 110 of FIGS. 14 and 15 have constructions as shown in FIGS. 18 and 17, respectively. In FIG. 18, pulse sensor 102 is mounted on a board 105, and a housing 108 is provided with a dustproof and waterproof window 107 opposite to a detection surface of pulse sensor 102. A board 115 mounted by a pulse sensor 113 is sandwiched between external and internal cloths 118 and 117 forming finger cuff 112, exposing pulse sensor 113 through internal cloth 117.

The pulsimeter 100 of FIG. 14, however, has the disadvantages that the insufficiency of shading due to the construction of pulse sensor 102 disposed on the face makes the pulsimeter easily subject to external lights, such as sunlight and fluorescent lamps, whereby the pulse number is measured erroneously or cannot be counted. The portion of finger's touch including dustproof and waterproof window 107 does not the configurations of the fingers well, and the sensitivity of pulse sensor 102 is lowered by window 107 covering the detection surface of pulse sensor 102 to reduce light passing therethrough, resulting in inaccurate measurement.

The pulsimeter 110 of FIG. 15 in which pulse sensor 113 is disposed on finger cuff 112 has good shading as compared with the pulsimeter of FIG. 14, but is still disadvantageous such that the shading is insufficient because the finger touch portion including pulse sensor 113 is hard to fit a peripheral configuration of a finger and sufficient contact area and pressure is not applied to pulse sensor 113 by the skin of finger. Accordingly, the measurement by the pulsimeter is inaccurate or impossible to be executed because the obtainable signal pulse is small. Moreover, since the finger is bound by finger cuff 112 during the measurement of pulse, the freedom of the finger is restricted and wrapping the cuff around finger is troublesome. The wire 114 connecting cuff 112 with the main body is obstructive for carrying the cuff with pulsimeter 110, and separate carriage of finger cuff 112 and wire 114 is also troublesome.

SUMMARY OF THE INVENTION

In view of the above-mentioned disadvantages, it is a primary object of this invention to provide a pulsimeter having good shading against external light with improving the accuracy of pulse measurement.

It is another object of this invention to provide a pulsimeter additionally including a pedometer function for convenience use.

According to one aspect of this invention, there is provided a pulsimeter which includes a main body, a finger insertion section disposed on the main body in which a finger is inserted, a pulse sensor for sensing pulses of a finger inserted into the finger insertion section, and a display for displaying the pulses sensed by the pulse sensor, the finger insertion section being disposed on a surface different from a surface provided with the display. Since the finger insertion section is located on a surface different from a display surface on which the display is disposed and the display surface is directed to be located on the front face of the pulsimeter in a normal pulse measurement, the finger insertion section is hard to be intruded by external light and lowering a pulse measurement accuracy is reduced.

According to a further aspect of this invention, there is provided a pulsimeter which includes a main body, a finger insertion section disposed on the main body in which a finger, a pulse sensor for sensing pulses of a finger is inserted into the finger insertion section, and a display for displaying the pulses sensed by the pulse sensor, the finger insertion section being covered with an elastic hood. The hood covering the finger insertion section provides an improved shading against external light and makes a pulse value be sensed with accuracy. Moreover, the hood is elastic, whereby it is well fitted with a finger in any size and the finger is properly pressed to the detection surface of the pulse sensor.

According to a still further aspect of this invention, there is provided a pulsimeter which includes a main body, a finger insertion section disposed on the main body to be inserted by a finger, a pulse sensor for sensing pulses of a finger inserted into the finger insertion section, a display for displaying the pulses sensed by the pulse sensor, the pulse sensor being airtightly held by an elastic pressing member and a sensing surface of the sensor being exposed to the finger insertion section. Since the pulse sensor is airtightly held by an elastic pressing member and a sensing surface of the sensor is exposed to the finger insertion section, the main body can be free from entry of dust or water and the like and, upon insertion of a finger to the finger insertion section, the finger comes into a direct contact with the detection surface of the pulse sensor to provide a sufficient sensitivity.

As the finger insertion section is further so designed that the direction of insertion by a finger is in a vertical direction of the main body but oblique to a horizontal direction of the main body, the finger is easy to be inserted into the finger insertion section, unnecessary force is not applied to the finger on measurement, and there is provided an excellent construction in view of human engineering, typically when the pulsimeter is attached to a belt of the user's pants for convenient use, like a pedometer.

The main body internally includes a printed circuit board mounted by various electronic components. By disposing the display on one surface of the board to provide a display unit and the pulse sensor directly on the opposite surface, a space or chamber within the main body can be fully utilized to reduce the pulsimeter in size. Such utilization of space can be performed by arranging the display on the front face and the finger insertion section on the different face of the main body.

By designing the finger insertion section opposite to the hood to have a recessed cross-section, the finger inserted into the finger insertion section is brought into a position such that the thick of the finger comes into contact with the recessed section in association with the elastic hood to improve tight contact between the finger and the recessed section. In other words, the thick portion of the finger is curved in a convex shape, so that employing configuration in the finger insertion section along with the configuration of the thick of finger can precisely fit the finger into the finger insertion section until the tip of the finger, resulting in the improvement of contact between the finger and the detection surface of the pulse sensor disposed in the finger insertion section.

When a construction for sandwiching a housing of the main body with the hood is employed, mounting the hood on the finger insertion section can be done only by sandwiching the housing with one end of the hood, resulting in easy assembling of the pulsimeter and sufficient shading in a mounting portion.

For the purpose of easy insertion of finger, the hood made of a finger smooth material is desirable to insert the finger into the finger insertion section without any resistance. Typically, the flexible material of hood may be a flexible cloth or spandex.

According to another aspect of this invention, there is provided a meter for counting pulses and steps which includes a pulse sensor for sensing pulses, a vibration sensor, a display, and a controller for displaying a counted value of output of the pulse sensor and/or output of the vibration sensor. As appreciated, a pedometer is often used by being attached to a belt of a skirt or pants. The meter according to this aspect serves as a pulsimeter and a pedometer, and is convenient when it is used like a pedometer.

The use similar to a pedometer can be performed in this invention by employing a portable member (for example, buckle or clip) associated with the main body. Moreover, as the main body includes an open-and-close cover for protecting the display and the cover includes a portable member, the convenience of use is further improved.

As described above, the pulsimeter according to this invention may be not only a meter having a pulse measurement function but also a meter having a pulsimeter function and a pedometer function. The meter having pulsimeter and pedometer functions houses components of a pedometer function within a main body and has a modified arrangement of an internal circuit construction and a display design according to the additional pedometer function, while retaining outlook of the meter.

BRIEF DESCRIPTION OF THE DRAWINGS

Other objectives and advantages of this invention will be more readily apparent from the following detailed description provided in conjunction with the following figures, of which:

FIG. 12 is a schematic circuit block diagram of a meter having both pulsimeter and pedometer functions as another embodiment;

FIG. 13 typically shows an example of a step display in the display of the pulsimeter;

FIG. 14 shows a conventional pulsimeter and one example of use thereby;

DETAILED DESCRIPTION OF THE INVENTION

Figure 1:
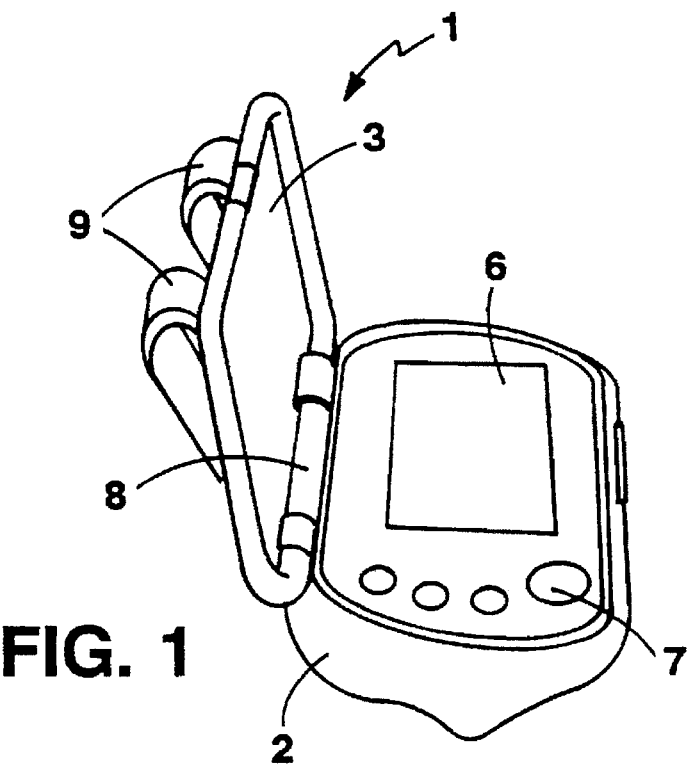
FIG. 1 is a perspective external view of a pulsimeter as a primary embodiment of this invention.
Figure 2:
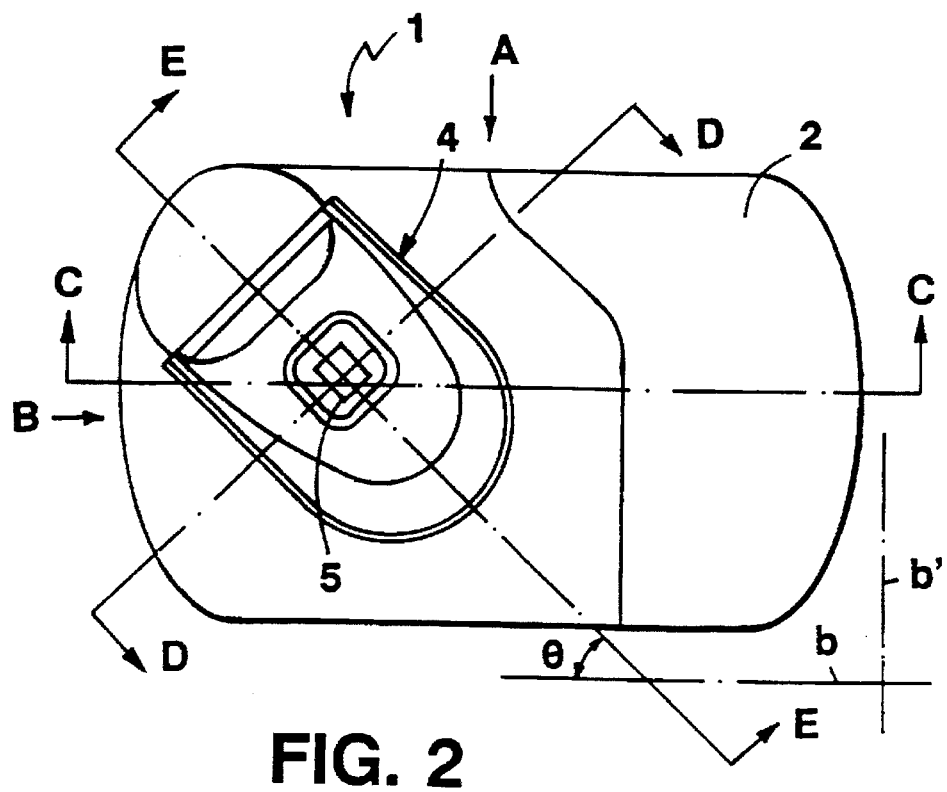
FIG. 2 is a plane view of a reverse side of a main body of the pulsimeter of FIG. 1.
Figure 3:
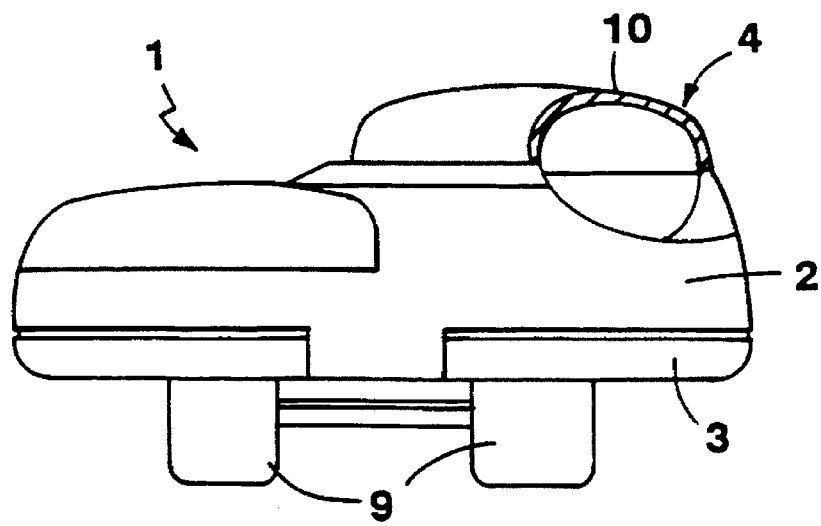
FIG. 3 is a side view of the pulsimeter viewed from a direction marked by an arrow marked A in FIG. 2.
Figure 4:
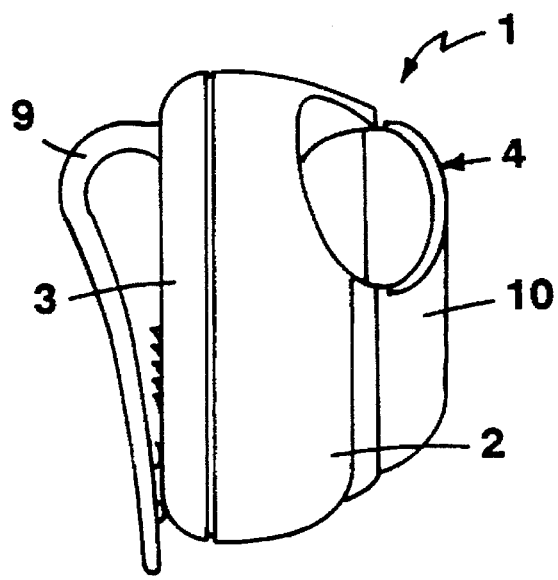
FIG. 4 is a side view of the pulsimeter viewed from a direction marked by an arrow marked B in FIG. 2.

Referring, now, to FIG. 1, there is shown a pulsimeter 1 as a primary embodiment of this invention. FIG. 1 shows a perspective external view of the pulsimeter, FIG. 2 shows a plane view of a reverse side of a main body of the pulsimeter, FIG. 3 shows a side view of the pulsimeter viewed from a direction marked by an arrow mark A in FIG. 2, and FIG. 4 shows a side view of the pulsimeter viewed from a direction marked by an arrow mark B in FIG. 2. The pulsimeter 1 includes a main body 2 and a cover 3. The main body 2 is provided with a finger insertion section 4 into which a finger is inserted, a pulse sensor 5 for sensing the pulses of the finger inserted into section 4, and a display 6 for displaying the pulses sensed by the sensor 5. In FIG. 1, the display 6 is disposed on a front face of the main body 2, and a switch 7 is disposed by the side of the display 6. Cover 3 is disposed to protect the front face (including display 6) of the main body, and engaged with the main body through a hinge connector 8 in a open and close relationship. Moreover, in this embodiment, a buckle 9, serving as a member for portable use disposed on the face of cover 3 to be attached to a belt of pants, skirt or the like to carry the pulsimeter 1.

In FIG. 2, finger insertion section 4 is disposed on the reverse side of main body 2, viz., on the opposite side of body 2 to the display 6, and includes a hood 10 (see FIG. 3) made of a flexible cloth (e.g., spandex) which is smooth against finger. As shown in FIG. 2, finger insertion section 4 is disposed to have an insertion direction "a" slanting by an angle θ with respect to a horizontal direction "b" of body 2 and by an angle "90°−θ" with respect to a vertical direction "b'". In practice, angle θ is recommended to be about 20° to 50°, and in this embodiment about 45° is employed. This angle θ is employed considering that slant insertion to finger insertion section 4 makes the insertion of a finger much easier than parallel or vertical insertion about the horizontal direction "b" in view of human engineering when the pulsimeter 1 is assumed to be attached to a belt of pants or the like for its use like a pedometer.

Figure 5:
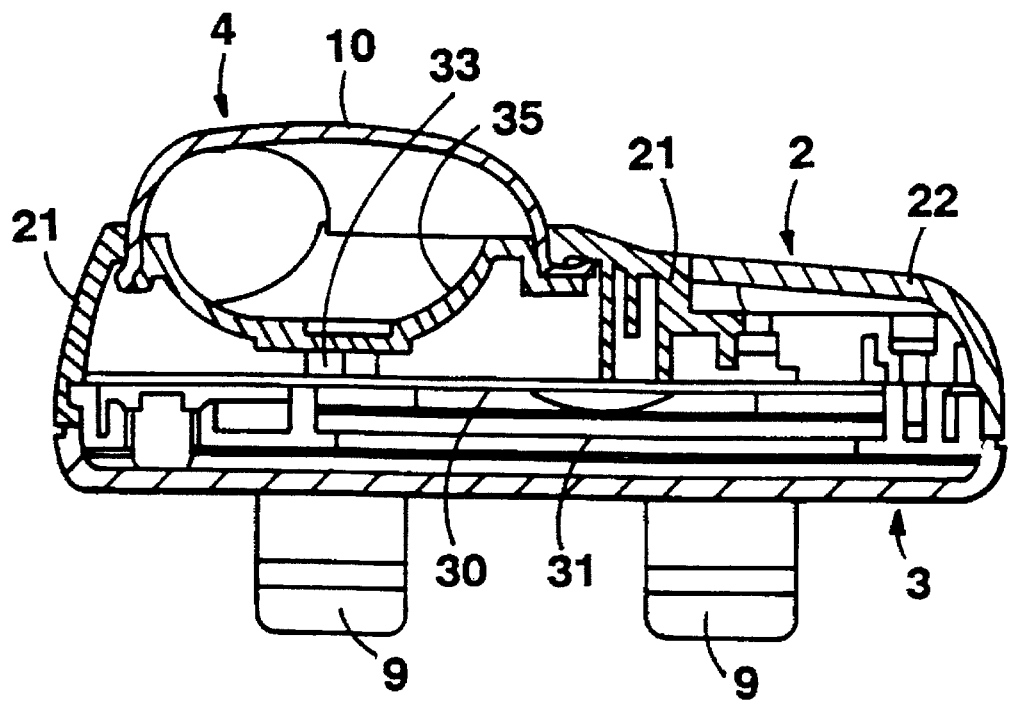
FIG. 5 is a sectional view of the pulsimeter taken along the line C—C shown in FIG. 2.
Figure 6:
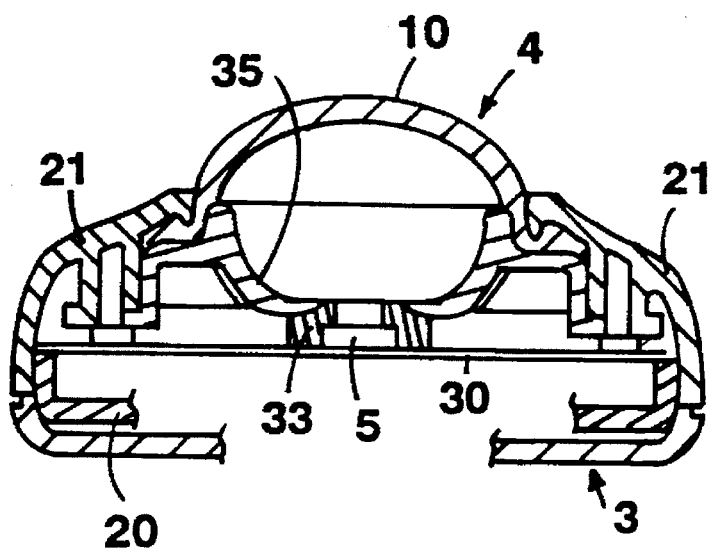
FIG. 6 is a sectional view of the pulsimeter taken along the line D—D shown in FIG. 2.
Figure 7:
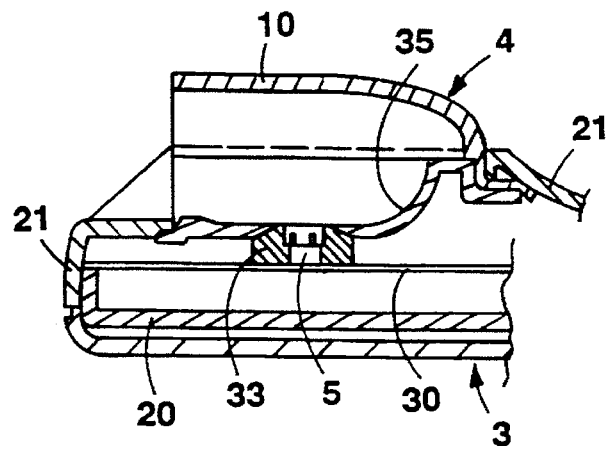
FIG. 7 is a sectional view of the pulsimeter taken along the line E—E shown in FIG. 2.

In FIG. 5 showing internal construction of body 2 (a sectional view along the line C—C shown in FIG. 2), FIG. 6 (a sectional view along the line D—D shown in FIG. 2) and FIG. 7 (a sectional view along the line E—E shown in FIG. 2), the main body 2 includes a lower housing 20 and an upper housing 21 which is engaged with lower housing 20 and includes a battery cover 22 as a part of upper housing 21 for an attachable-and-removal engagement therewith.

A liquid crystal display (LCD) 31 is arranged on a front side (display side) of a board 30 disposed within body 2, and a pulse sensor 5 is arranged on an reverse side of the board. Thus, mounting electronic components on both sides of the board 30 efficiently utilizes a chamber within body 2. Pulse sensor 5 consists of a light emitting element (typically, infrared radiation LED) and a light receiving element (typically, phototransistor). The both elements are molded with synthetic resin into a single unit, and airtightly held at a predetermined position of a holder base 35 providing finger insertion section 4 by a flexible pressing member or a sponge 33 having a predetermined proper rigidity. Sponge 33 is partially sandwiched with holder base 35 to be fixed at a predetermined position to hold sensor 5 airtightly. A detection surface of pulse sensor 5 is leveled with a surface of holder base 35, exposing through base 35. Thus, the pulse sensor 5 is airtightly held by elastic pressing member 33 and the sensing surface of sensor 5 is exposed to finger insertion section 4, the main body 2 can be free from entry of dust or water and, upon insertion of a finger to finger insertion section 4, the finger comes into a direct contact with the detection surface of pulse sensor 5 to provide a precise pulse measurement.

As shown in FIG. 6 about finger insertion section 4, hood 10 has a configuration having a convex cross section and hold base 35 has recessed cross section, whereby upon inserting a finger into finger insertion section 4, the finger is properly pushed by hood 10 toward holder base 35, the thick portion of the finger is driven into a tight contact with a recessed portion of holder base 35, and the contact between the inserted finger and the detection surface of sensor 5 is ensured. Thus, a stable accuracy of pulse measurements is guaranteed for any size of fingers. One end of hood 10 is tightly sandwiched by upper housing 21 and holder base 35 so as to avoid causing hood 10 to come of such a sandwich construction. The construction for sandwiching hood 10 by housing 21 and base 35 makes hood 10 easily mountable in finger insertion section 4 and provides satisfactory shading in attaching components.

Figure 8:
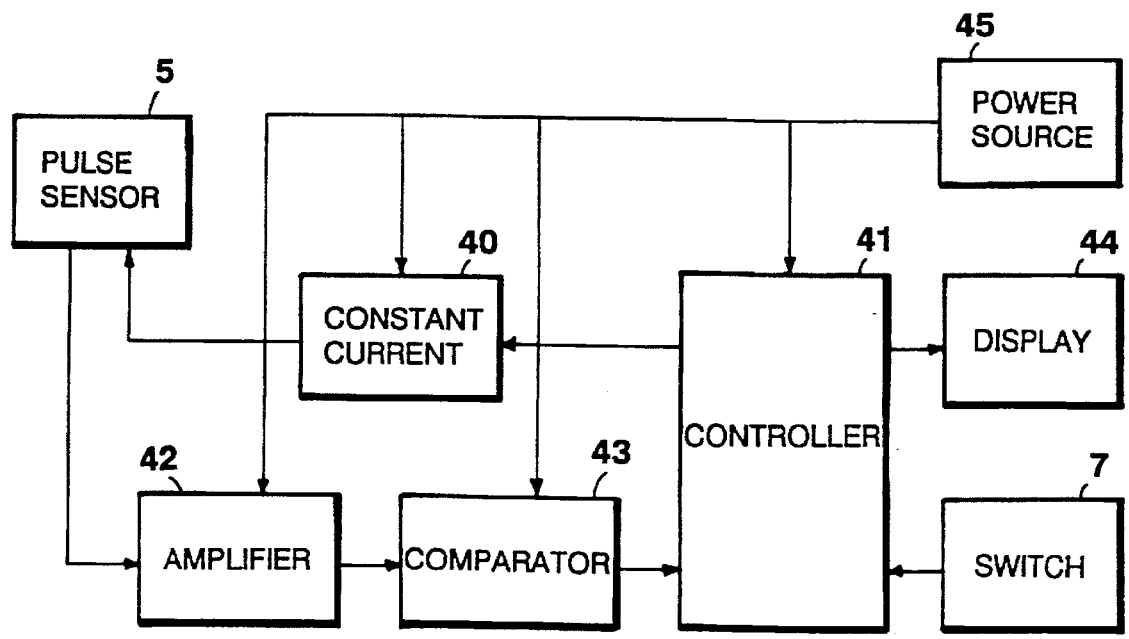
FIG. 8 is a schematic circuit block diagram of the pulsimeter.

In FIG. 8 there is shown a circuit of the pulsimeter 1. A constant current circuit 40 supplies the light emitting element of pulse sensor 5 with a current but is controlled by a control circuit 41. The control circuit 41 employs a microcomputer and peripheral circuit components to control ON/OFF operation of the light emitting element, detection of pulse signals, computation of pulse number, display of the computed pulse number, and so forth. An amplifier 42 amplifies signals sensed by the light receiving element of pulse sensor 5, and a comparator 42 extracts pulse synchronized signals from the amplified pulse signals. A display circuit 44 is disposed to display the number of pulses obtained by this pulsimeter, and may also display the number of steps in case that the pulsimeter is required to further include a pedometer function. A power source circuit 45 consists of a dry cell or the like, serving as a source for the pulsimeter 1. A switch 7 for power supply is disposed on the front face of body 2 (FIG. 1) to turn on and off the pulsimeter.

Figure 9:
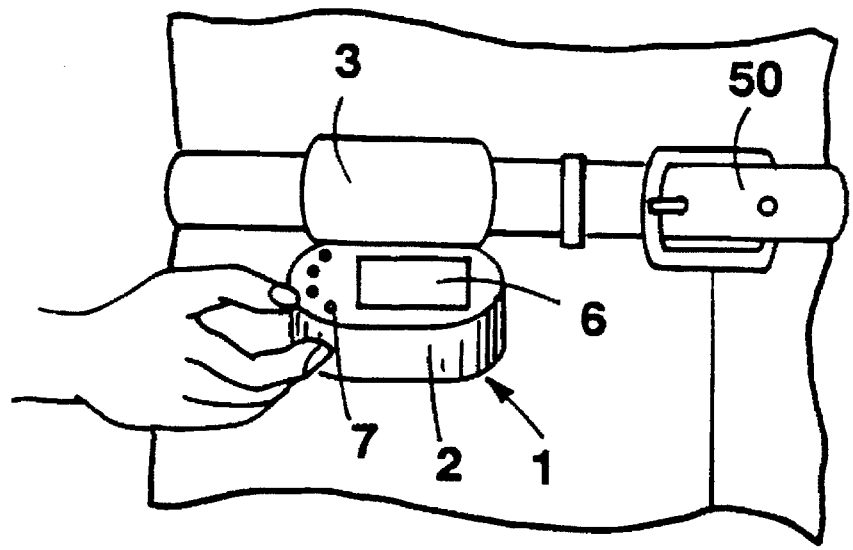
FIG. 9 shows one example of measurement of the pulsimeter which is mounted.

As shown in FIG. 9, thus constructed pulsimeter 1 is used by attaching buckle 9 disposed on cover 3 to belt 50 of pants or skirt. In a pulse measurement, main body 2 is detached from cover 3 to fall forward, and typically a forefinger of an operator is inserted into finger insertion section 4, supporting main body 2 with another hand. Then, switch 7 while is pushed to turn on power source 45 though such pushing the switch may be made prior to insertion of the finger. Upon pushing switch 7, pulses are automatically detected to be indicated on display 6. After completion of the pulse measurement, switch 7 is pushed again to turn off the power source, and cover 3 is moved to return to main body 2 for closing. Though the portable member 9 is disposed on the cover 3 in this embodiment, it may be disposed on the main body 2. Moreover, the display 6 may be disposed on the cover 3 instead of the main body 2, if desired.

Figure 10:
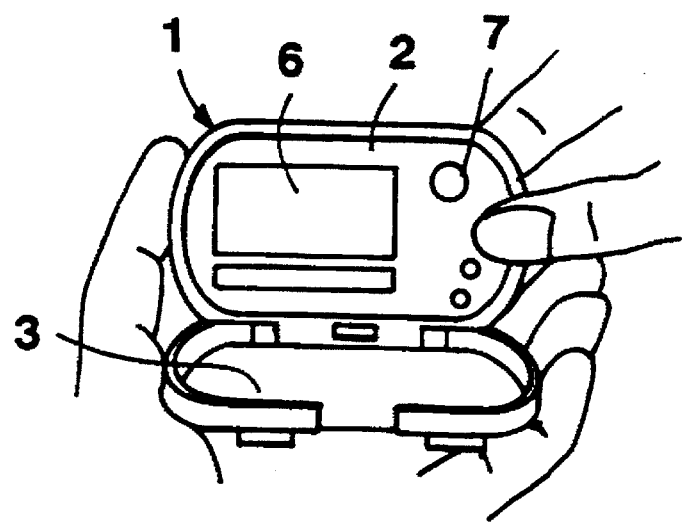
FIG. 10 shows another example of measurement by the pulsimeter.

Though pulsimeter 1 is attached to belt 50 in this embodiment, it may be put into a breast pocket or carried by putting it into other pocket or a bag, if desired. Moreover, the pulse measurement may be executed without being attached to the belt, if desired. Typically, as shown in FIG. 10, the pulsimeter 1 may be held by one hand, and a finger of another hand may be inserted into finger insertion section 4.

Figure 11A:
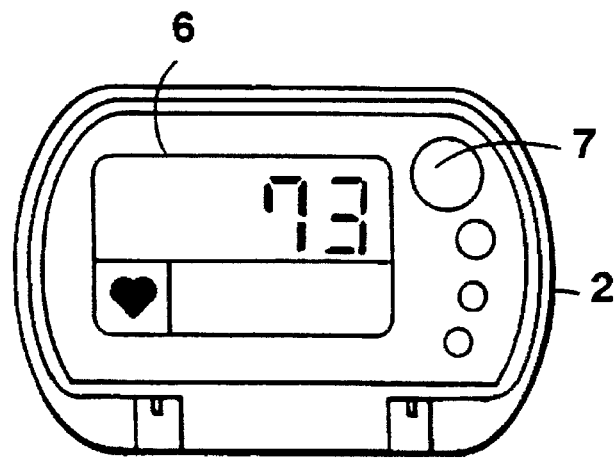
FIG. 11 shows an example of display modes in the display of the pulsimeter.
Figure 11B:
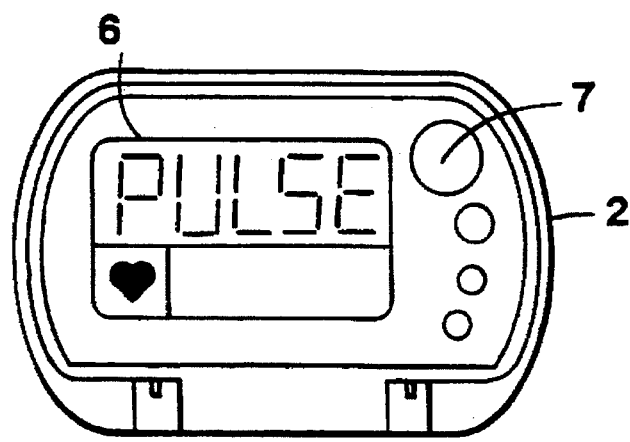
Figure 11C:
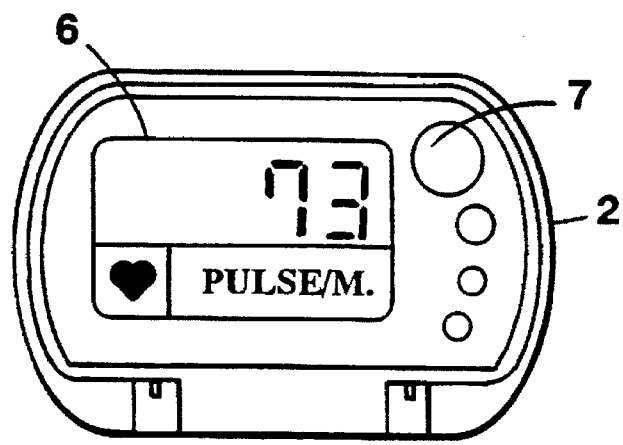
Figure 15A:
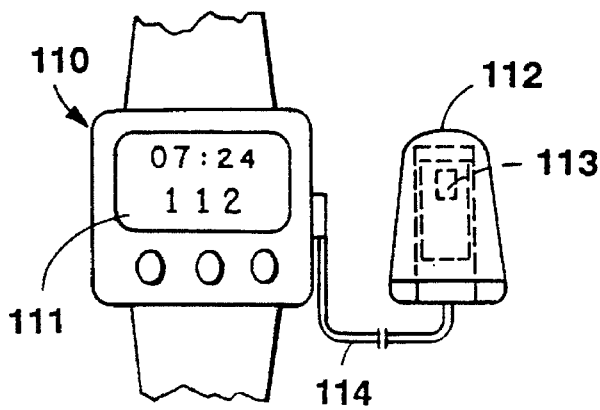
FIG. 15 shows another conventional pulsimeter and one example of use thereby.
Figure 15B:
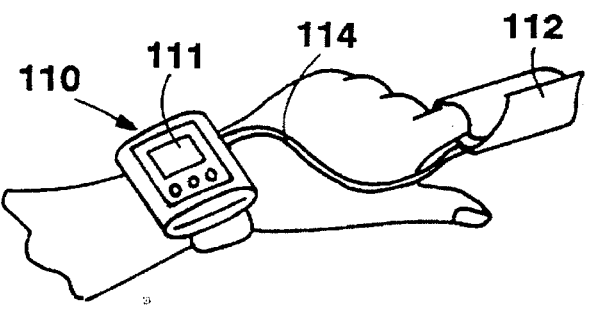
Figure 16:
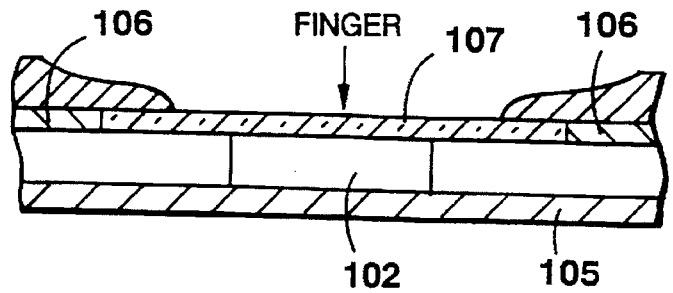
FIG. 16 is a sectional view of a pulse sensor portion of the pulsimeter of FIG. 14.
Figure 17:
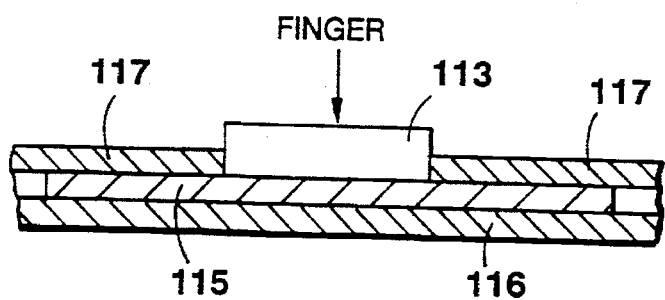
FIG. 17 is a sectional view of a pulse sensor portion of the pulsimeter of FIG. 15.

In FIG. 11, a display operation is exemplarily shown. In absence of a push operation to switch 7, the display shows a state of in FIG. 11(a). Upon pushing switch 7, an indication "PULSE" meaning a stand-by state for measurement is displayed on display 6 as shown in FIG. 11(b). Upon inserting a finger into finger insertion section 4 in this stand-by state, pulses are sensed by pulse sensor 5 to display the number of pulses a minute as typically shown in FIG. 11(c). If switch 7 is pushed in the display state shown in FIG. 11(b) or (c), the operation will be returned to the initial state shown in FIG. 11(a).

As mentioned above, the pulsimeter 1 of this embodiment may be modified to include a pedometer function in addition to the pulsimeter function, if desired. For this modification, the main body may enclose therewithin components for a step measurement, such as a vibration sensor and so forth, and the associated circuits and display may be modified as shown in FIGS. 12 and 13 without changing the external configuration of the main body. This modified pulsimeter is shown in FIGS. 12 and 13.

FIG. 12 shows a block diagram of the modified pulsimeter, where the same components as those of FIG. 8 are represented by the same reference numerals and their explanation is omitted for a simplified explanation. The pulsimeter provided with a pedometer function further includes a vibration sensor 61, an amplifier 62 for amplifying output signals from vibration sensor 61, a comparator and counter circuit 63 for comparing an output signal from amplifier 62 with a predetermined set value or discriminating the output signal by level to count the number of signals larger than the predetermined value. Power source circuit 45 supplies amplifier 62 and circuit 63 with power. A control circuit 141 has a pedometer function in addition to the pulsimeter function of the circuit 41 of FIG. 8. According to the pedometer function of circuit 141, upon actuating a mode switch 64, the number of steps represented by a counted value in the comparator and counter circuit 63 is applied to display circuit 44 instead of the number of pulses.

Upon actuating the switch 64, the number of pulses is again applied to display circuit 44. Thus, on each actuation to switch 64, the numbers of walking steps and heart pulses are alternatively displayed. Though the switch 64 employs a push button switch, it may employ a slide switch to select pulsimeter or pedometer mode by sliding button of the switch, if desired. In this modification, upon turning on the power by switch 7, control circuit 141 resets the counted value of the comparator and counter circuit 63. The counting and storing function executed by the circuit 63 may be executed by control circuit 141 by further modification. The display alternatively indicating the numbers of pulses and steps may be modified to simultaneously indicate both numbers.

While the invention has been described and illustrated with respect to certain embodiments which give satisfactory results, it will be understood by those skilled in the art, after understanding the purpose of the invention, that various other changes and modifications may be made without departing from the spirit and scope of the invention, and it is therefore intended in the appended claims to cover all such changes and modifications.

What is claimed is:

1. A pulsimeter comprising:

a main body having a front face and a back face opposite the front face, a finger insertion section disposed on the back face of said main body into which a finger is insertable, a pulse sensor for sensing pulses of a user's finger inserted into said finger insertion section, and a display disposed on the front face of said main body and configured to display a number of pulses per minute sensed by said pulse sensor, wherein said display and said finger insertion section are arranged such that said display may be observed by the user while the user's finger is inserted into said finger insertion section.

\* \* \* \* \*